(12) United States Patent
Liu

(10) Patent No.: US 12,251,302 B2
(45) Date of Patent: *Mar. 18, 2025

(54) FULL DEPTH OF FOCUS INTRAOCULAR LENS

(71) Applicant: Alcon Inc., Fribourg (CH)

(72) Inventor: Yueai Liu, Arlington, TX (US)

(73) Assignee: Alcon Inc., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/357,441

(22) Filed: Jul. 24, 2023

(65) Prior Publication Data

US 2024/0000561 A1    Jan. 4, 2024

Related U.S. Application Data

(63) Continuation of application No. 16/381,359, filed on Apr. 11, 2019, now Pat. No. 11,751,990.

(60) Provisional application No. 62/656,400, filed on Apr. 12, 2018.

(51) Int. Cl.
*A61F 2/16* (2006.01)

(52) U.S. Cl.
CPC .......... *A61F 2/1618* (2013.01); *A61F 2/1621* (2013.01); *A61F 2/1654* (2013.01); *A61F 2002/1683* (2013.01)

(58) Field of Classification Search
None
See application file for complete search history.

(56) References Cited

U.S. PATENT DOCUMENTS

| 8,480,228 | B2 | 7/2013 | Weeber | |
|---|---|---|---|---|
| 2007/0182924 | A1* | 8/2007 | Hong | G02C 7/06 351/159.43 |
| 2009/0088840 | A1* | 4/2009 | Simpson | G02C 7/042 623/6.11 |
| 2011/0098811 | A1* | 4/2011 | Hong | A61F 2/1654 623/6.27 |

* cited by examiner

*Primary Examiner* — Javier G Blanco
(74) *Attorney, Agent, or Firm* — Patterson + Sheridan, LLP

(57) ABSTRACT

An ophthalmic lens comprising an anterior surface and a posterior surface, at least one of the anterior surface and posterior surface including a first surface region corresponding to a photopic aperture of a pupil and a second surface region corresponding to a difference between the photopic aperture and a mesopic aperture of the pupil. A first microstructure pattern formed in a the first surface region, the first microstructure pattern introducing a phase perturbation into an optical path of incoming light such that a full depth of focus for photopic vision is provided.

8 Claims, 9 Drawing Sheets

INTRAOCULAR LENS (IOL)

OCULAR LENS APERTURES OF THE PUPIL

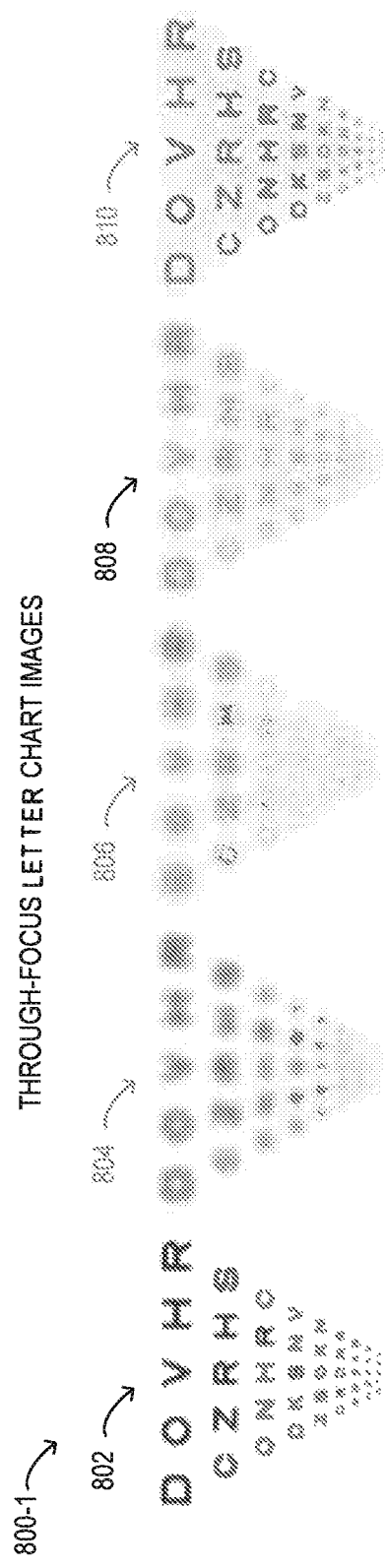
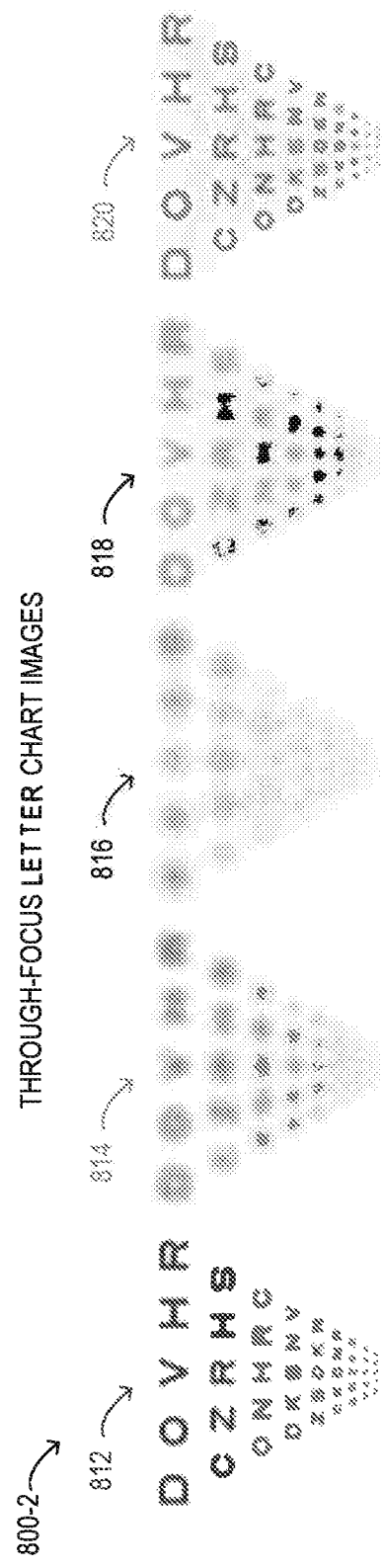
FIG. 8A
FIG. 8B

FULL DEPTH OF FOCUS INTRAOCULAR LENS

CROSS-REFERENCE TO RELATED APPLICATION

This application is a continuation of U.S. application Ser. No. 16/381,359, filed Apr. 11, 2019, which claims priority to and the benefit of U.S. Provisional Patent Application No. 62/656,400, filed Apr. 12, 2018. The aforementioned applications are incorporated by reference herein in their entirety, and are hereby expressly made a part of this specification.

FIELD

The present disclosure relates generally to ophthalmic lenses and more specifically to a presbyopia-correcting full depth of focus ophthalmic lens.

BACKGROUND

The human eye includes a cornea and a crystalline lens that are intended to focus light that enters the pupil of the eye onto the retina. However, the eye may exhibit various refractive errors which result in light not being properly focused upon the retina, and which may reduce visual acuity. Ocular aberrations can range from the relatively simple spherical and cylindrical errors that cause myopia, hyperopia, or regular astigmatism, to more complex refractive errors that can cause, for example, halos and starbursts in a person's vision.

Many interventions have been developed over the years to correct various ocular aberrations. These include spectacles, contact lenses, corneal refractive surgery, such as laser-assisted in situ keratomileusis (LASIK) or corneal implants, and intraocular lenses (IOLs). The diagnosis and specification of sphero-cylindrical spectacles and contact lenses for treatment of myopia, hyperopia, and astigmatism are also well-established.

Presbyopia describes a condition in which the human eye loses the ability to clearly see objects at a close distance. Ophthalmic lenses with multifocal capabilities have been developed to help patients focus on objects at a relatively close distance.

In particular, IOLs have been developed with multifocal capabilities that allow patients to focus simultaneously at two or three focal planes. However, multifocal IOLs typically are not able to provide a full range of vision from near to infinite distance.

IOLs have also been developed with extended depth of focus (EDF) capabilities. However, the extension of the depth of focus is far too limited to fully correct for presbyopia in patients. Accordingly, there is a need for a system and method that provides depth of focus extension that provides a Full Depth of Focus (FDoF) continually from near to infinite distance.

SUMMARY

In certain embodiments, an ophthalmic lens comprising an anterior surface and a posterior surface, at least one of the anterior surface and posterior surface including a first surface region corresponding to a photopic aperture of a pupil and a second surface region corresponding to a difference between the photopic aperture and a mesopic aperture of the pupil. A first microstructure pattern formed in a the first surface region, the first microstructure pattern introducing a phase perturbation into an optical path of incoming light such that a full depth of focus for photopic vision is provided.

In certain embodiments, the second surface region may be refractive. Alternatively, a second microstructure pattern may be formed in the second surface region. In certain embodiments, the second microstructure pattern may comprising a bifocal diffractive structure or a trifocal diffractive structure.

BRIEF DESCRIPTION OF THE DRAWINGS

For a more complete understanding of the present invention and its features and advantages, reference is now made to the following description, taken in conjunction with the accompanying drawings, in which:

FIGS. 8A and 8B show through focus images at mesopic aperture corresponding to the microstructure shown in FIG. 7A and a typical bifocal lens, respectively;

DETAILED DESCRIPTION

Figure 1:
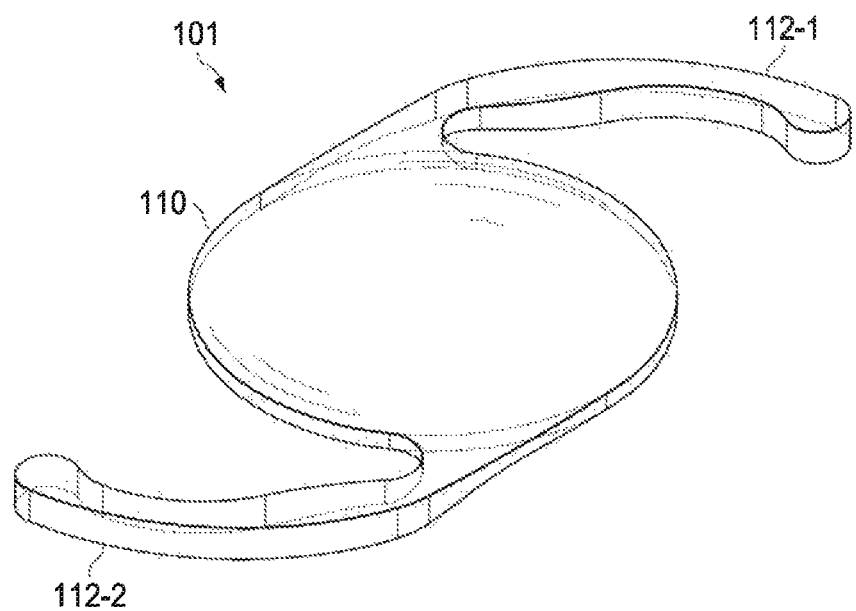
FIG. 1 is a depiction of an exemplary IOL.

The exemplary embodiments relate to ophthalmic devices such as IOLs and contact lenses. The following description is presented to enable one of ordinary skill in the art to make and use the invention and is provided in the context of a patent application and its requirements. Various modifications to the exemplary embodiments and the generic principles and features described herein will be readily apparent.

The exemplary embodiments are mainly described in terms of particular methods and systems provided in particular implementations. However, the methods and systems will operate effectively in other implementations. For example, the method and system are described primarily in terms of IOLs. However, the method and system may be used with contact lenses and spectacle glasses.

In the following description, details are set forth by way of example to facilitate discussion of the disclosed subject matter. It should be apparent to a person of ordinary skill in the field, however, that the disclosed embodiments are exemplary and not exhaustive of all possible embodiments.

As used herein, a hyphenated form of a reference numeral refers to a specific instance of an element and the un-hyphenated form of the reference numeral refers to the collective element. Thus, for example, device '12-1' refers to an instance of a device class, which may be referred to collectively as devices '12' and any one of which may be referred to generically as a device '12'.

After cataract treatment or human natural lens replacement with a conventional monofocal IOL, the patient's vision becomes presbyopic. Conventional solutions have involved either multifocal intraocular lens (MIOL) designs or extended depth of focus (EDF) designs. Some bifocal IOLs can provide patients with good vision simultaneously at far and near distances, however, patients implanted with such a bifocal lens will generally have unsatisfactory intermediate distance vision. When a bifocal IOL with additional refractive power for intermediate distance ranges is used, a better intermediate distance vision may result but at the cost of poorer near distance vision. Certain trifocal IOLs may provide patients with a degree of far, intermediate, and near distance vision, albeit with a lack of continuity of vision from far to near distances. Typical EDF IOLs have limited depth of focus to intermediate distance vison, while near distance vision of a patient using an EDF IOL may still be compromised. Thus, as noted above, conventional multifocal IOLs are not able to provide presbyopia-correcting full range of vision from near to infinite distance.

As will be described in further detail, a full depth of focus IOL is disclosed that correct presbyopia and provide a full range of vision from near to infinite distance. The full depth of focus IOL disclosed herein may provide a high efficiency of light energy usage, indicating that the IOL is resistant to potential optical disturbances. The full depth of focus IOL disclosed herein may be implemented using refractive, bifocal, and trifocal designs in the region beyond the photopic aperture, and can provide vision that approximates monofocal, bifocal, or trifocal mesopic vision. The full depth of focus IOL disclosed herein may restore a full range of vision after replacement of the human crystalline lens.

A diffractive ophthalmic lens, such as the full depth of focus IOL disclosed herein, may be configured based upon the optical apertures. The ophthalmic lens may have an anterior surface, a posterior surface, and at least one diffractive structure consisting of a plurality of echelettes. A diffractive structure(s) may be located on either the anterior surface or the posterior surface. The diffractive structure(s) may provide a presbyopia-correcting full depth of focus for the ophthalmic lens at the photopic aperture while providing various kinds of performance characteristics for the mesopic aperture according to the different embodiments of the diffractive structure(s).

For example, diffractive structures located in the photopic aperture may result in various photopic through-focus performances, such as distance dominated, near dominated, or any other desired performance characteristics. The diffractive structures located in the photopic aperture may be combined with a second diffractive structure in the region beyond the photopic aperture and within the mesopic aperture. For example, the second diffractive structure may be null, meaning that it only provides refractive performance and provides monofocal-like through-focus performance in the mesopic aperture of the ophthalmic lens. For further example, the second diffractive structure may be a bifocal structure and may provide bifocal-like through-focus performance in the mesopic aperture of the ophthalmic lens. For yet another example, the second diffractive structure may be a trifocal structure and may provide trifocal-like through-focus performance in the mesopic aperture of the ophthalmic lens.

Referring now to the drawings, in FIG. 1, IOL 101 may represent any kind of IOL used in ophthalmology. As shown, IOL 101 includes an optic zone 110 (also referred to herein as simply an 'optic') and two haptics 112-1, 112-2, which are shown in an exemplary configuration for descriptive purposes. In various implementations, IOL 101 may include different types and numbers of haptics 112. In some implementations, IOL 101 may have no haptics. The materials used for optic zone 110 and haptics 112 may vary. For example, IOL 101 may be a non-foldable rigid IOL, such as with optic zone 110 comprising a polymethyl methacrylate (PMMA) lens. In some implementations, IOL 101 may be a flexible IOL, in which optic zone 110 may be comprised of various materials, such as silicone, hydrophobic acrylic, hydrophilic acrylic, hydrogel, collamer or combinations thereof. In IOL 101, haptics 112 may also be comprised of various materials, such as polypropylene, PMMA, hydrophobic acrylic, hydrophilic acrylic, silicone or combinations thereof. The optic zone 110 may be designed to have a specified optical refraction, or may be designed as a multifocal element with a plurality of optical refraction powers.

In particular, optic zone 110 may be implemented with a full depth of focus IOL that corrects presbyopia and provides a full range of vision from near to infinite distance. Accordingly, the present disclosure is directed to a microstructure incorporated on one surface of a normal refractive monofocal IOL optic. The microstructure is formed as a pattern within the same material as the base IOL optic itself. The microstructure introduces a phase perturbation into an optical path of incoming photons resulting in a presbyopia-correcting, extra-long extension of the depth of focus property of the IOL optic. For example, the depth of focus is extended from a far or infinite distance continuously to a near distance. The phase perturbation may be limited to a central region of the lens aperture to provide patient with a full depth of field photopic vision, as described by the apertures in FIG. 2 below.

Figure 2:
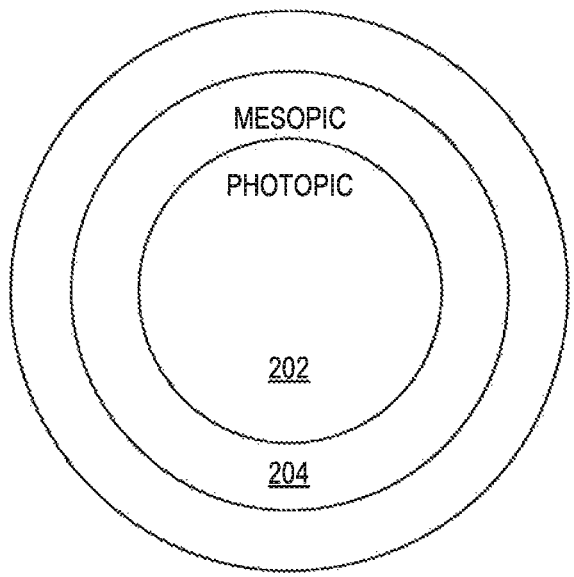
FIG. 2 is a depiction of different pupil apertures.

The phase perturbation may be distributed in a number of discontinuous concentric regions and may be different in different regions in the IOL aperture (see FIG. 2). Thus, the full depth of focus IOL may offer pupil size dependent performance to meet different needs of photopic and mesopic vision.

Referring now to FIG. 2, a depiction of ocular lens apertures 200 of the pupil are shown. A photopic aperture 202 indicates a pupil aperture under well lit conditions, such as in daylight conditions or at ambient light intensities of about 3 candelas/square meter ($cd/m^2$) or higher. A mesopic aperture 204 is larger than photopic aperture 202 and indicates a pupil aperture under dimly lit conditions, such as under moonlight or at ambient light intensities between about 3 $cd/m^2$ and about 0.01 $cd/m^2$. The full depth of focus IOL disclosed herein may be implemented with a microstructure surface pattern that is formed in the material of optic zone 110 at a location corresponding to photopic aperture 202 and mesopic aperture 204, as described in further detail below.

Figure 3A:
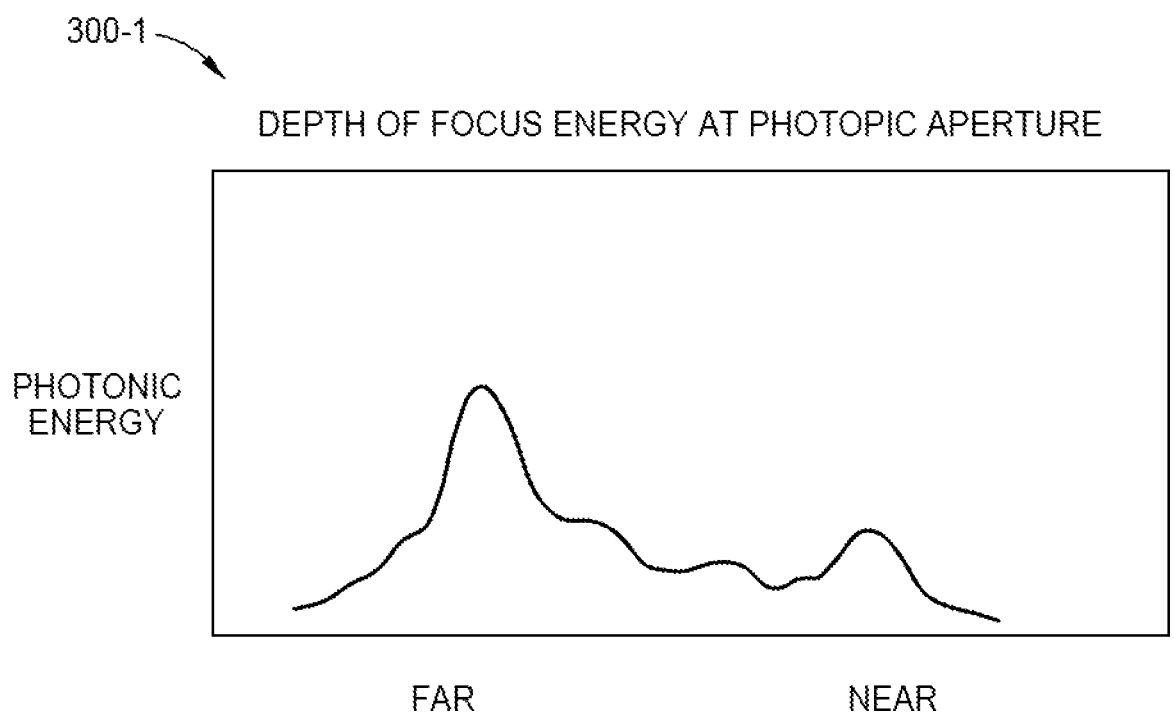
FIGS. 3A and 3B show plots of through focus energy distribution at photopic aperture with distance dominant and near dominant characteristics, respectively.
Figure 3B:
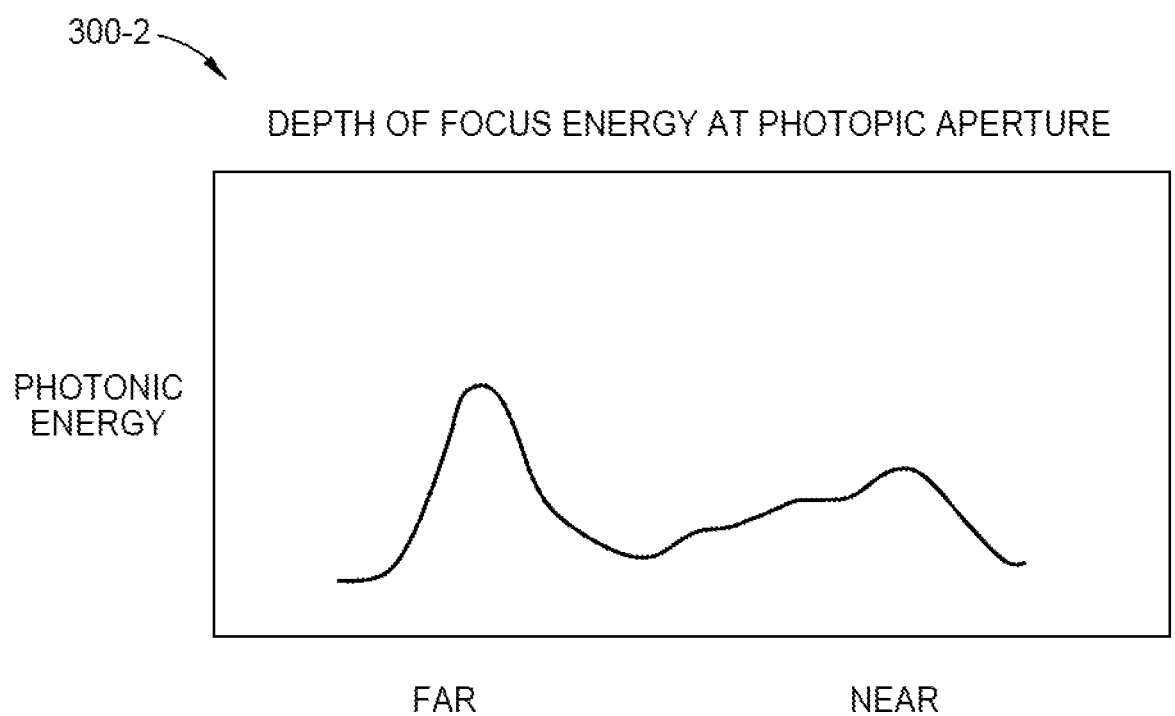

As noted, the phase perturbation in the photopic aperture of the full depth of field IOL may provide presbyopia-correcting full depth of focus photopic vision. FIGS. 3A and 3B illustrate two types of photopic energy through focus distributions resulting from the two different types of phase perturbation designs described in detail below and shown in FIG. 7A and FIG. 9A, respectively.

Referring now to FIG. 3A, a through focus energy plot 300-1 versus the depth of focus is shown. In plot 300-1, photonic energy is plotted against the defocus depth and shows how the photonic energy is distributed over far distances to near distances. In particular, it may be observed that plot 300-1 shows a far distance dominated energy curve that provides photopic vision with continuous depth of focus from far distances to near distances (see also FIG. 4A).

Referring now to FIG. 3B, a through focus energy plot 300-2 versus the depth of focus is shown. In plot 300-2, photonic energy is plotted against the defocus depth and shows how the photonic energy is distributed over far distances to near distances. In particular, it may be observed that plot 300-2 shows a near distance dominated energy curve that provides photopic vision with continuous depth of focus from far distances to near distances (see also FIG. 4B).

Figure 4A:
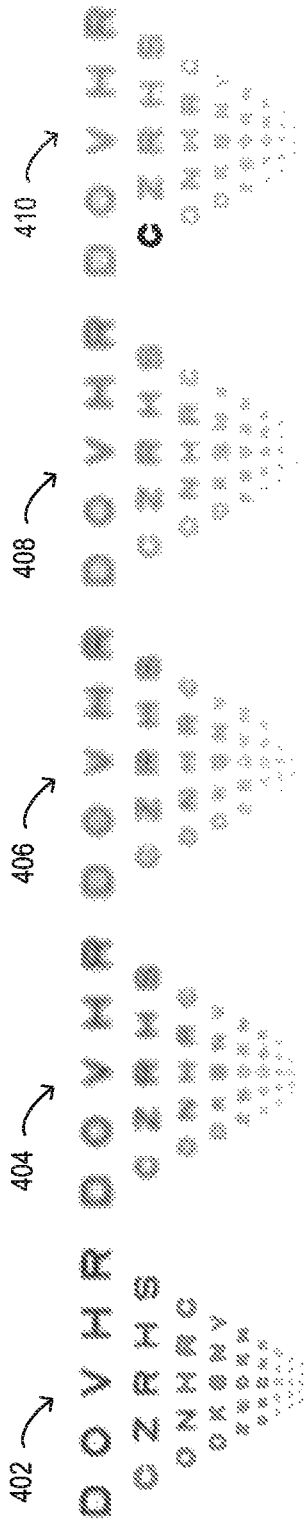
FIGS. 4A and 4B show through focus images at photopic aperture corresponding to the plots shown in FIGS. 3A and 3B, respectively.

Referring now to FIG. 4A, through focus letter chart images 400-1 are shown for the lens design corresponding to through focus energy plot 300-1. The five chart images in FIG. 4A respectively correspond to the defocus distances in Table 1.

TABLE 1

Defocus distances for through focus letter chart images

| Distance | Distance Description |
|---|---|
| ∞ | Far |
| 160 cm | Far-intermediate |
| 80 cm | Intermediate |
| 53 cm | Intermediate-near |
| 40 cm | Near |

The letter chart images in FIG. 4A correspond to the distances in Table 1 respectively: chart image 402—Far; chart image 404—Far-intermediate; chart image 406—Intermediate; chart image 408—Intermediate-near; and chart image 410—Near. Chart images 400-1 show that the depth of focus is continuous over the shown range of distances.

Figure 4B:
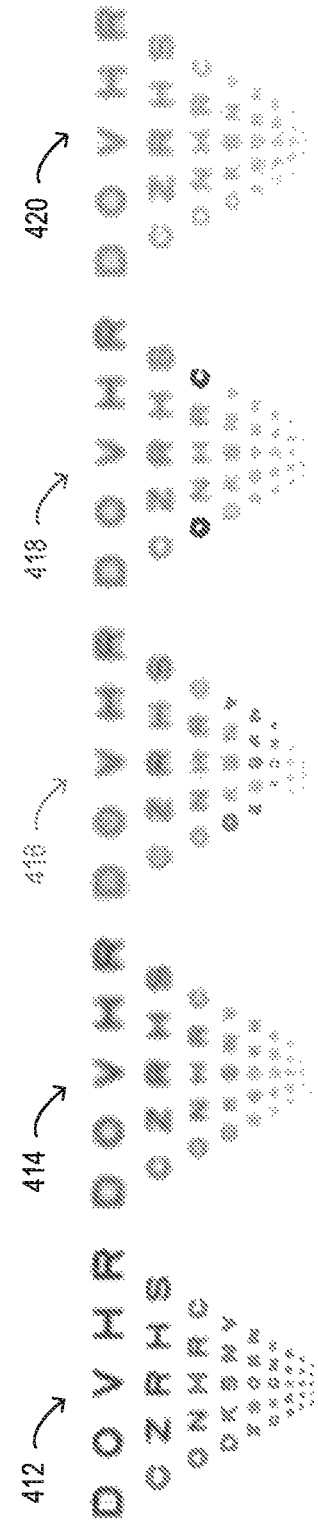

Referring now to FIG. 4B, through focus letter chart images 400-2 are shown for the lens design corresponding to through focus energy plot 300-2. The five chart images in FIG. 4B respectively correspond to the defocus distances in Table 1: chart image 412—Far; chart image 414—Far-intermediate; chart image 416—Intermediate; chart image 418—Intermediate-near; and chart image 420—Near. Chart images 400-2 show that the depth of focus is continuous over the shown range of distances.

Figure 5A:
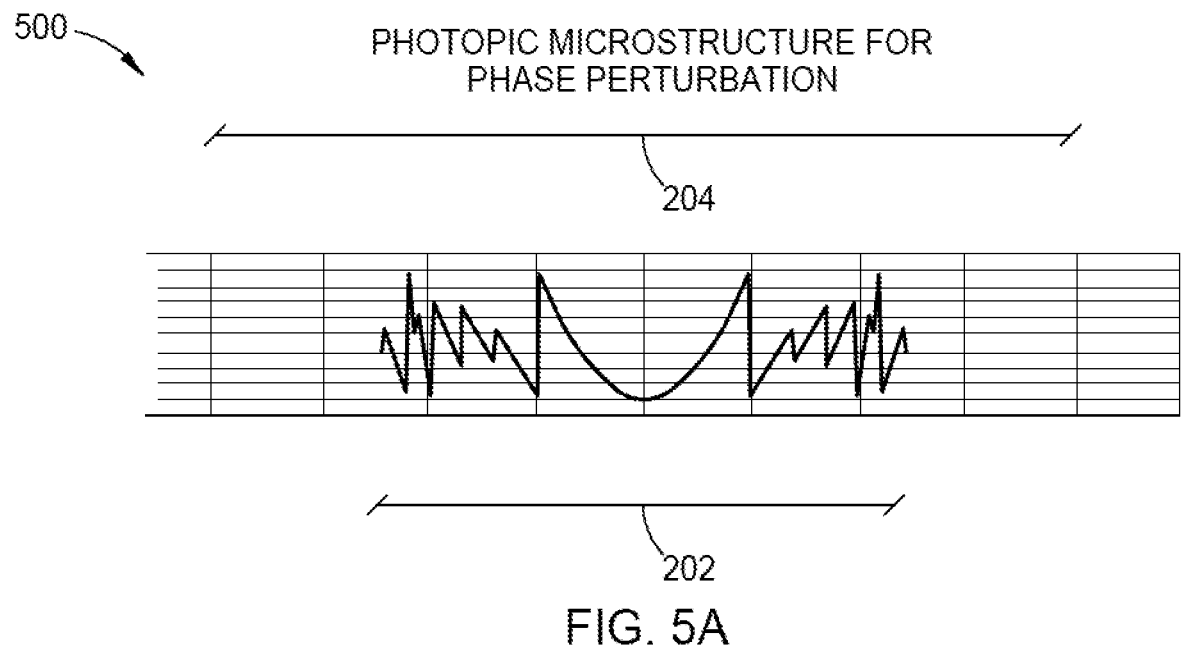
FIG. 5A is a depiction of a cross-section of a photopic microstructure for phase perturbation that is refractive beyond the photopic aperture.

Referring now to FIG. 5A, a photopic full depth of focus (FDoF) microstructure 500 is shown as a cross-sectional surface profile. Photopic FDoF microstructure 500 extends over photopic aperture 202, but does not extend beyond photopic aperture 202 to mesopic aperture 204. At the locations between photopic aperture 202 and mesopic aperture 204, normal refractive correction occurs. For the region outside the photopic aperture (RoPA), photopic microstructure 500 provides refractive power to provide monofocal-like mesopic vision. Accordingly, photopic FDoF microstructure 500 may limit the phase perturbation to photopic aperture 202, and there may be no phase perturbation beyond the photopic aperture 202.

Figure 5B:
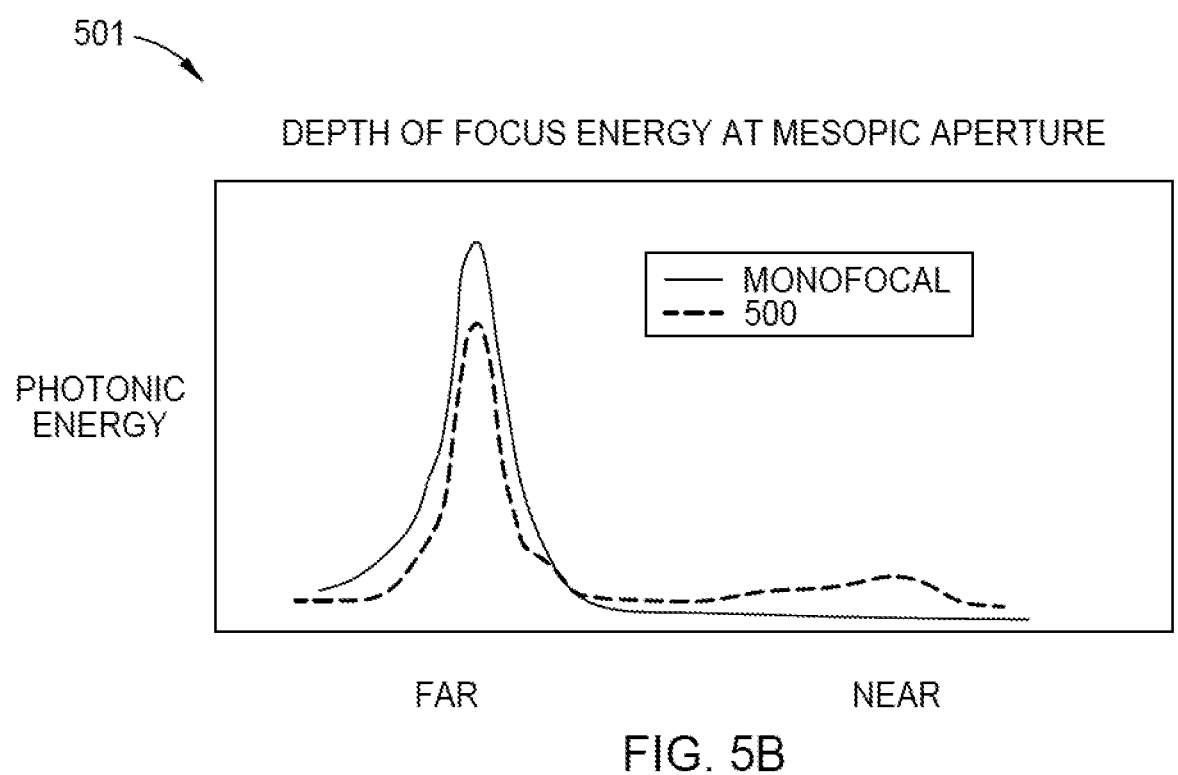
FIG. 5B shows a plot of through focus energy distribution at mesopic aperture corresponding to the microstructure shown in FIG. 5A in comparison to the through focus mesopic energy distribution corresponding to a typical monofocal lens.

Referring now to FIG. 5B, a through focus energy plot 501 versus the depth of focus is shown for photopic microstructure 500 (see FIG. 5A). In plot 501, photonic energy is plotted against the defocus distance and shows how the photonic energy is distributed over far distances to near distances. In particular, it may be observed that plot 501 shows a similarity to a monofocal lens but also provides more energy to near distances than a monofocal lens.

Figure 6A:
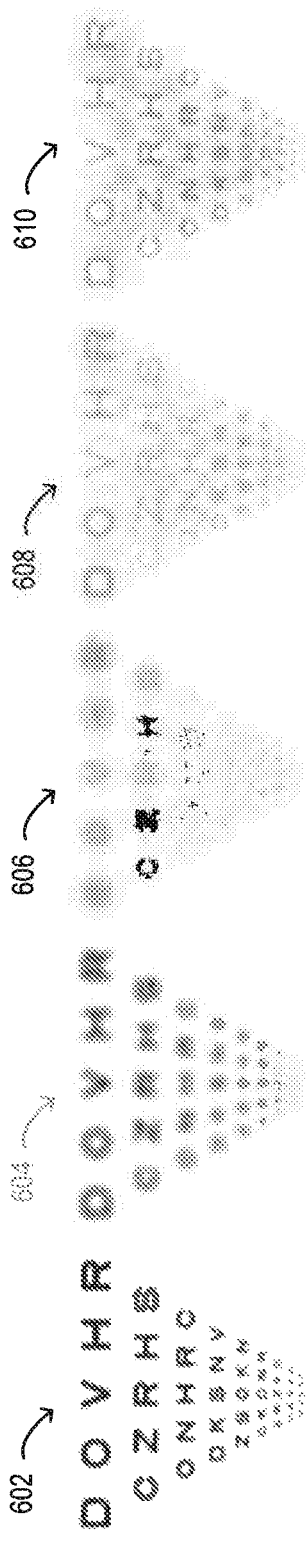
FIGS. 6A and 6B show through focus images at mesopic aperture corresponding to the microstructure shown in FIG. 5A and a typical monofocal lens, respectively.

Referring now to FIG. 6A, mesopic aperture through focus letter chart images 600-1 are shown for the monofocal design of photopic microstructure 500, as shown in through focus energy plot 501. The five chart images in FIG. 6A respectively correspond to the defocus distances in Table 1: chart image 602—Far; chart image 604—Far-intermediate; chart image 606—Intermediate; chart image 608—Intermediate-near; and chart image 610—Near. Chart images 600-1 show that far image 602 has a monofocal quality while a moderately continuous depth of focus is maintained, especially for near distances.

Figure 6B:
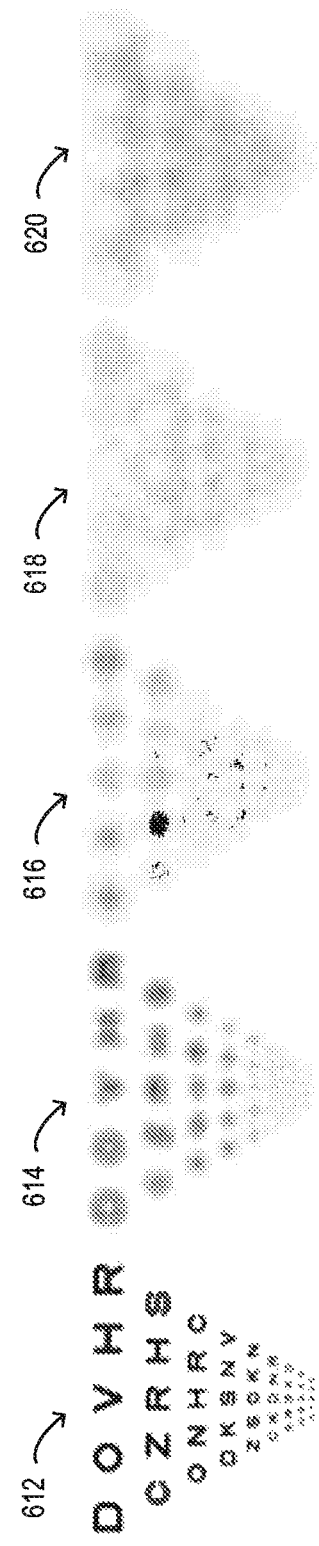

Referring now to FIG. 6B, through focus letter chart images 600-2 are shown for a conventional monofocal IOL, as shown in through focus energy plot 501. The five chart images in FIG. 6B respectively correspond to the defocus distances in Table 1: chart image 612—Far; chart image 614—Far-intermediate; chart image 616—Intermediate; chart image 618—Intermediate-near; and chart image 620—Near. Chart images 600-2 show that far image 612 has a monofocal quality while no depth of focus is maintained, in direct contrast to chart images 600-1.

Figure 7A:
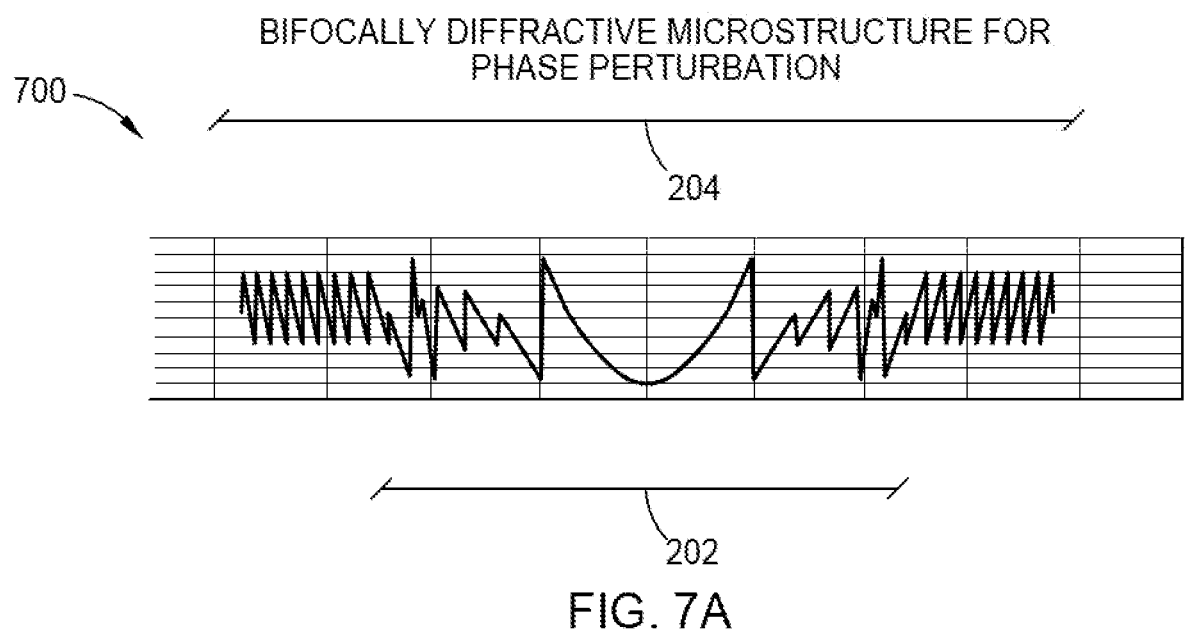
FIG. 7A is a depiction of a cross-section of a diffractive microstructure for phase perturbation that includes a bifocal diffractive microstructure beyond the photopic aperture.

Referring now to FIG. 7A, a FDoF-bifocally diffractive microstructure 700 is shown as a cross-sectional surface profile. FDoF-bifocally diffractive microstructure 700 extends over photopic aperture 202 and exhibits FDoF characteristics therein and extends beyond photopic aperture 202 to mesopic aperture 204 and exhibits bifocal characteristics therein. FDoF-bifocally diffractive microstructure 700 may result in a FDoF photopic vision, as illustrated in FIG. 4A or FIG. 4B, and a bifocal-like mesopic vision. The phase perturbation beyond photopic aperture 202 takes the form of a bifocal design. The step height, width, and phase values of the bifocal design may be optimized for the desired through focus energy distribution according to the design method and procedure described in detail below.

Figure 7B:
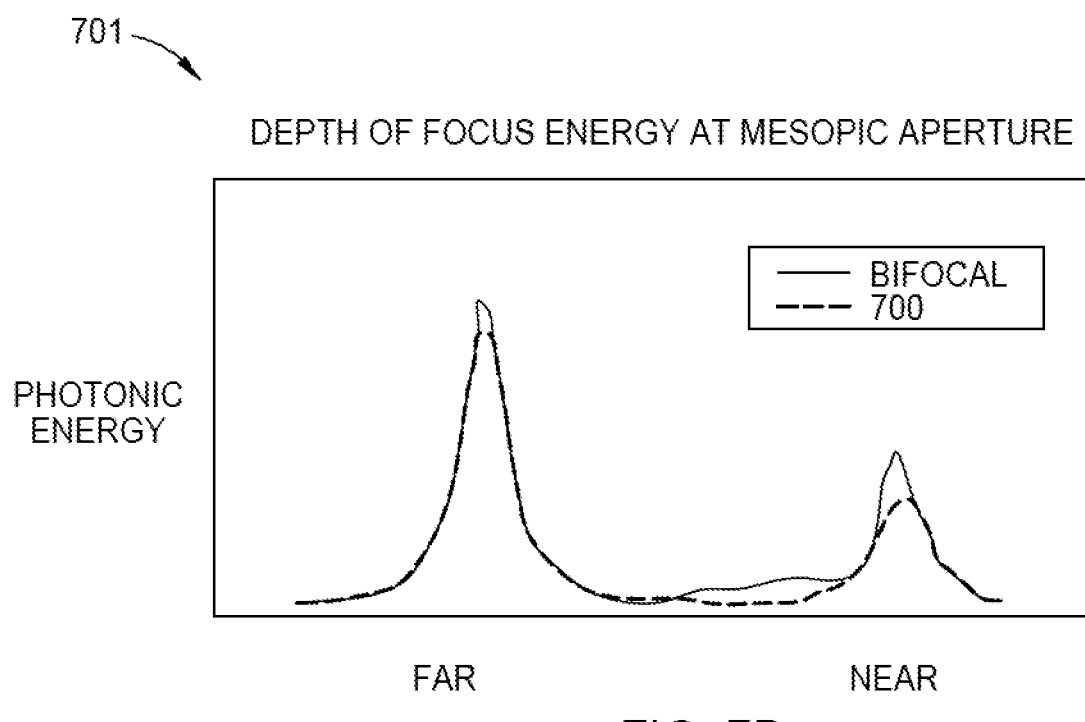
FIG. 7B shows a plot of through focus energy distribution at mesopic aperture corresponding to the microstructure shown in FIG. 7A in comparison to the through focus mesopic energy distribution corresponding to a typical bifocal lens.

Referring now to FIG. 7B, a through focus energy plot 701 versus the depth of focus is shown for FDoF-bifocally diffractive microstructure 700 (see FIG. 7A). In plot 701, photonic energy is plotted against the defocus distance and shows how the photonic energy is distributed over far distances and near distances. In particular, it may be observed that plot 701 shows a corresponding mesopic performance of the specific phase perturbation shown in FIG. 7A. In plot 701, two focal points are discernable through the depth of focus, one for far distance vision and the other for near distance vision, and the correlation with a bifocal lens is evident.

Referring now to FIG. 8A, mesopic aperture through focus letter chart images 800-1 are shown for the FDoF-bifocally diffractive microstructure 700, as shown in through focus energy plot 701. The five chart images in FIG. 8A respectively correspond to the defocus distances in Table 1: chart image 802—Far; chart image 804—Far-intermediate; chart image 806—Intermediate; chart image 808—Intermediate-near; and chart image 810—Near. Chart images 800-1 show a mesopic imaging effect in that both far distance image 802 and near distance image 810 have high quality, while intermediate images at various levels of depth of focus are also formed with varied quality.

Referring now to FIG. 8B, through focus letter chart images 800-2 are shown for a conventional bifocal IOL, as shown in through focus energy plot 701. The five chart images in FIG. 8B respectively correspond to the defocus distances in Table 1: chart image 812—Far; chart image 814—Far-intermediate; chart image 816—Intermediate; chart image 818—Intermediate-near; and chart image 820—Near. Chart images 800-2 show both far distance image 812 and near distance image 820 have high quality, while intermediate images at various levels of depth of focus have poorer quality than chart images 800-1.

Figure 9A:
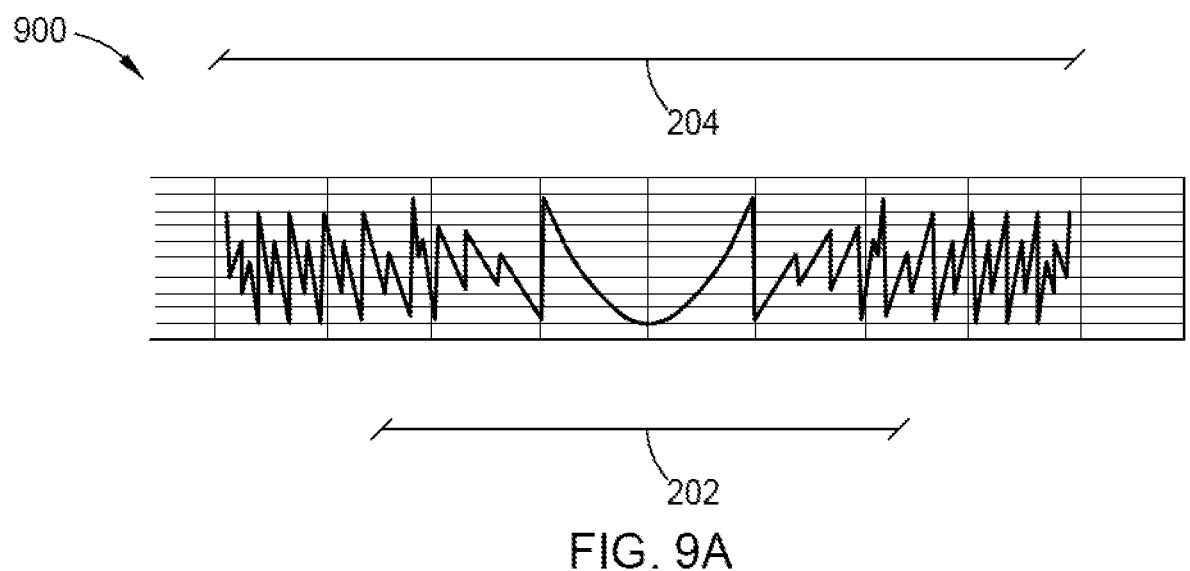
FIG. 9A is a depiction of a cross-section of a diffractive microstructure for phase perturbation that includes a trifocal diffractive microstructure beyond the photopic aperture.

Referring now to FIG. 9A, a FDoF-trifocally diffractive microstructure 900 is shown as a cross-sectional surface profile. FDoF-trifocally diffractive microstructure 900 extends over photopic aperture 202 and exhibits FDoF characteristics therein and extends beyond photopic aperture 202 to mesopic aperture 204 and exhibits trifocal characteristics therein. FDoF-trifocally diffractive microstructure 900 may result in a FDoF photopic vision, as illustrated in FIG. 4A or FIG. 4B, and a trifocal-like mesopic vision. The phase perturbation beyond photopic aperture 202 takes the form of a trifocal design. The step heights, widths, and phase values of the trifocal design may be optimized for the desired through focus energy distribution according to the design method and procedure described in detail below.

Figure 9B:
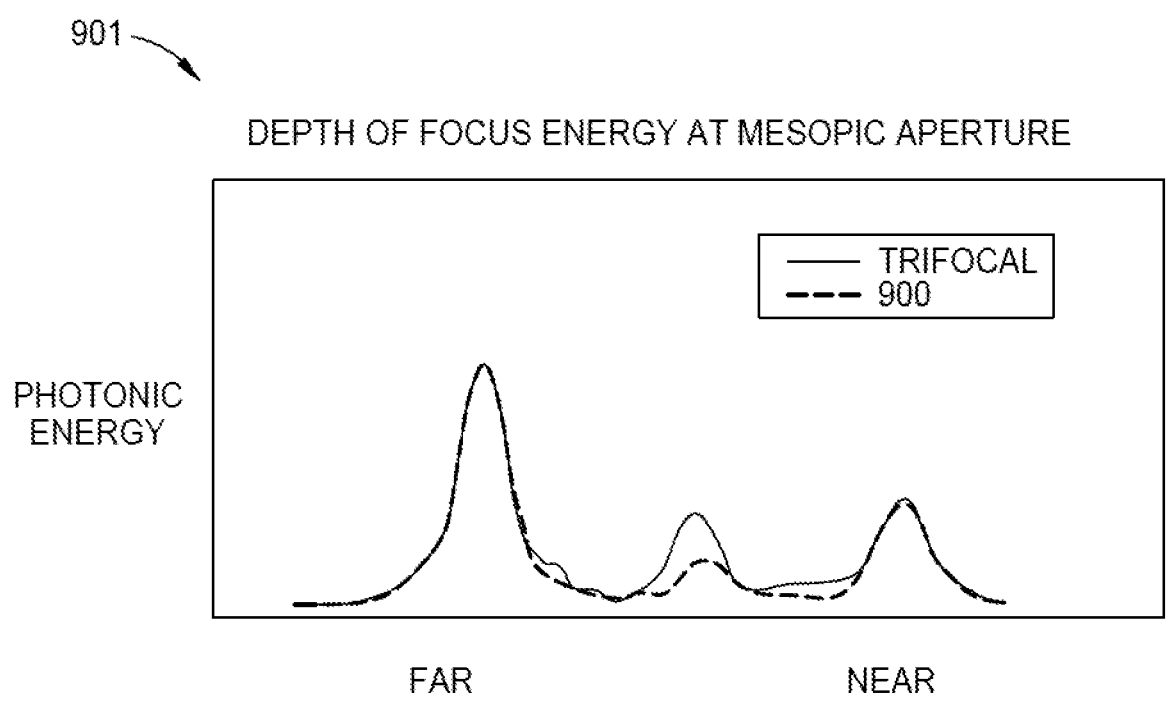
FIG. 9B shows a plot of through focus energy distribution at mesopic aperture corresponding to the microstructure shown in FIG. 9A in comparison to the through focus mesopic energy distribution corresponding to a typical trifocal lens.

Referring now to FIG. 9B, a through focus energy plot 901 versus the depth of focus is shown for FDoF-trifocally diffractive microstructure 900 (see FIG. 9A). In plot 901, photonic energy is plotted against the defocus distance and shows how the photonic energy is distributed over far distances to near distances. In particular, it may be observed that plot 901 shows a corresponding mesopic performance of the specific phase perturbation shown in FIG. 9A. In plot 901, three focal points are discernable through the depth of focus, one for far distance vision, another for intermediate distance vision, and yet another for near distance vision, and the correlation with a trifocal lens is evident.

Figure 10A:
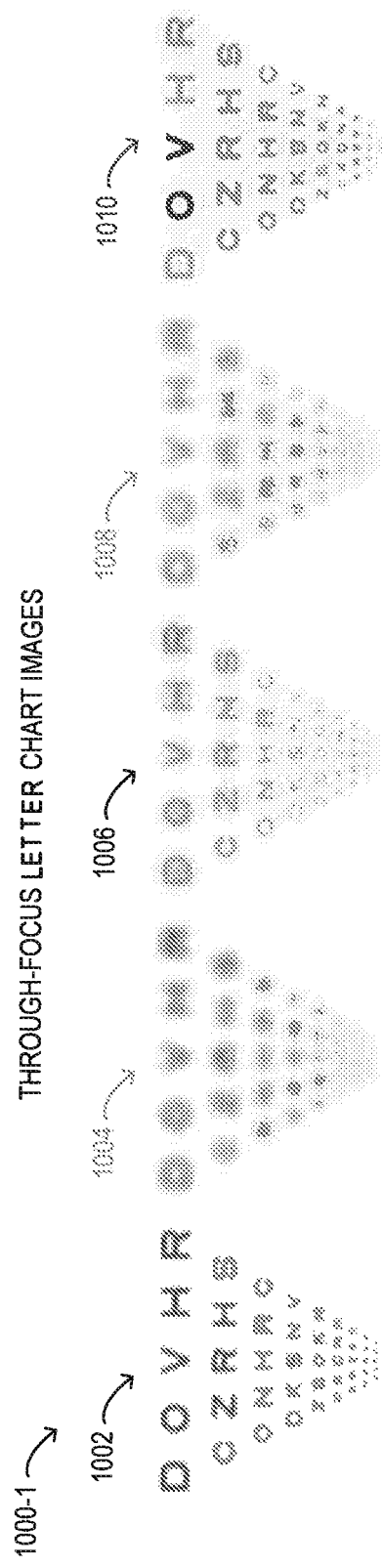
FIGS. 10A and 10B show through focus images at mesopic aperture corresponding to the microstructure shown in FIG. 9A and a typical trifocal lens, respectively.

Referring now to FIG. 10A, mesopic aperture through focus letter chart images 1000-1 are shown for the trifocal design of FDoF-trifocally diffractive microstructure 900, as shown in through focus energy plot 901. The five chart images in FIG. 10A respectively correspond to the defocus distances in Table 1: chart image 1002—Far; chart image 1004—Far-intermediate; chart image 1006—Intermediate; chart image 1008—Intermediate-near; and chart image 1010—Near. Chart images 1000-1 show a mesopic imaging effect in that far distance image 1002, intermediate distance image 1006, and near distance image 1010 have good or high quality, while other intermediate images at various levels of depth of focus are also formed with continuity of image quality.

Figure 10B:
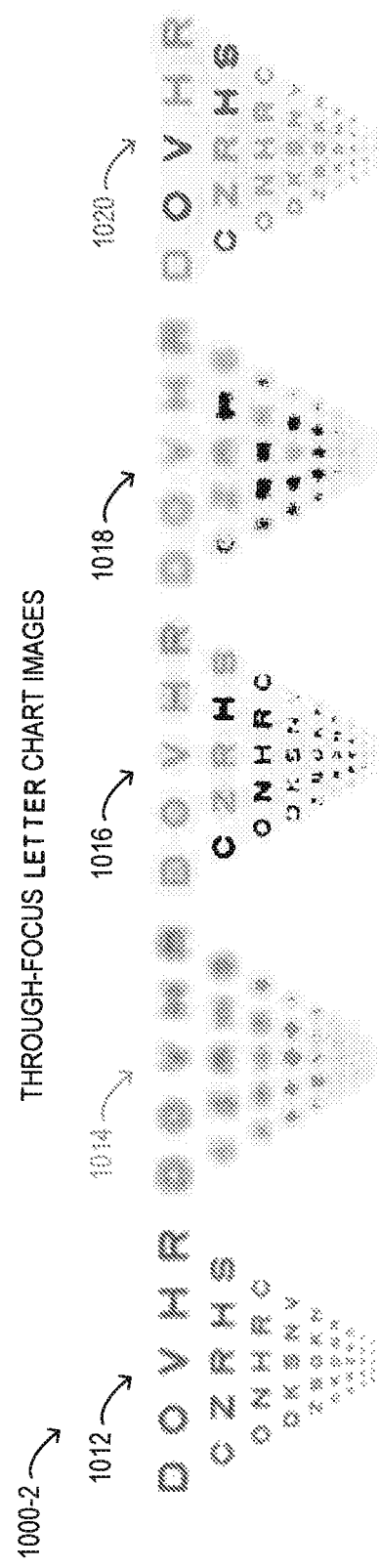

Referring now to FIG. 10B, through focus letter chart images 1000-2 are shown for a conventional trifocal IOL, as shown in through focus energy plot 901. The five chart images in FIG. 10B respectively correspond to the defocus distances in Table 1: chart image 1012—Far; chart image 1014—Far-intermediate; chart image 1016—Intermediate; chart image 1018—Intermediate-near; and chart image 1020—Near. Chart images 1000-2 show a mesopic imaging effect in that far distance image 1012, intermediate distance image 1016, and near distance image 1020 have good or high quality.

The FDoF photopic microstructure 500 shown in FIG. 5A, the FDoF-bifocally diffractive microstructure 700 shown in FIG. 7A, and the FDoF-trifocally diffractive microstructure 900 shown in FIG. 9A may all be designed according to the following method and procedure. A photopic microstructure, such as FDoF photopic microstructure 500, may be defined by a step pattern. The step pattern may be characterized by a number of parameters including, for example, a number of steps, a step height, a step width, and a phase value. A photopic microstructure may be designed with various numbers of steps. For example, FDoF photopic microstructure 500 is shown in FIG. 5A with six steps. However, a photopic microstructure may be designed with more than six steps or fewer than six steps. The other step parameters may also be selected to modify the through focus photopic aperture performance of the ophthalmic lens.

Once a photopic microstructure has been selected, the photopic microstructure may be optimized. For example, the performance of the photopic microstructure may be simulated using any suitable optical design software program, for example ZEMAX optical design software. During this optimization process, the through focus photopic aperture performance corresponding to the photopic microstructure may be calculated. A baseline through focus photopic aperture performance may also be determined and may represent the intended or target performance that is being sought through the design and optimization process. For example, the baseline through focus photopic aperture performance may be a far distance dominated performance or a near distance dominated performance. The through focus photopic aperture performance of the photopic microstructure may be compared to the baseline through focus photopic aperture performance. If the first through focus aperture performance does not adequately approximate the baseline through focus photopic aperture performance, the step parameters of the photopic microstructure may be adjusted.

Once the step parameters have been adjusted, a second through focus photopic aperture performance corresponding to the adjusted photopic microstructure may be calculated. The second through focus photopic aperture performance may then be compared to the baseline through focus photopic aperture performance. If the second through focus photopic aperture performance adequately approximates the baseline through focus photopic aperture performance, the adjusted photopic microstructure may be selected and implemented in the manufacturing and forming of an ophthalmic lens. However, if the second through focus photopic aperture performance does not adequately approximate the baseline through focus photopic aperture performance, the step parameters of the adjusted photopic microstructure may again be adjusted. In some instances, the first through focus photopic aperture performance may more closely approximate the baseline through focus photopic aperture performance than does the second through focus photopic aperture performance. In this case, the step parameters of the adjusted photopic microstructure may be adjusted accordingly. This process may be repeated as many times as necessary in order to provide a photopic microstructure with a through focus photopic aperture performance that adequately approximates the baseline through focus photopic aperture performance. Ultimately the photopic microstructure with the through focus photopic aperture performance that most closely approximates the baseline through focus photopic aperture performance may be selected and implemented in the manufacturing and forming of an ophthalmic lens.

A mesopic microstructure, such as FDoF-bifocally diffractive microstructure 700 in the mesopic aperture shown in FIG. 7A, and FDoF-trifocally diffractive microstructure 900 in the mesopic aperture shown in FIG. 9A, may be defined by a step pattern. The step pattern may be characterized by a number of parameters including, for example, a number of steps, a step height, a step width, and a phase value. A mesopic microstructure may be designed to provide various types of through focus mesopic aperture performances. For example, FDoF-bifocally diffractive microstructure 700 may be designed to approximate a bifocal through focus mesopic aperture performance and FDoF-trifocally diffractive microstructure 900 is designed to approximate a trifocal through focus mesopic aperture performance. However, a mesopic microstructure may be designed, through selection of the various step parameters, to approximate other through focus mesopic aperture performances.

Once a mesopic microstructure has been selected, the mesopic microstructure may be optimized. For example, the mesopic microstructure may be simulated using any suitable optical design software program, for example ZEMAX optical design software. During this optimization process, the through focus mesopic aperture performance corresponding to the mesopic microstructure may be calculated. A baseline through focus mesopic aperture performance may also be determined and may represent the intended or target performance that is being sought through the design and optimization process. For example, the baseline through focus mesopic aperture performance may be bifocal or trifocal performance as previously discussed. The through focus mesopic aperture performance of the mesopic microstructure may be compared to the baseline through focus mesopic aperture performance. If the first through focus mesopic aperture performance does not adequately approximate the baseline through focus mesopic aperture performance, the step parameters of the mesopic microstructure may be adjusted.

Once the step parameters have been adjusted, a second through focus mesopic aperture performance corresponding to the adjusted mesopic microstructure may be calculated. The second through focus mesopic aperture performance may then be compared to the baseline through focus mesopic aperture performance. If the second through focus mesopic aperture performance adequately approximates the baseline through focus mesopic aperture performance, the adjusted mesopic microstructure may be selected and implemented in the manufacturing and forming of an ophthalmic lens. However, if the second through focus mesopic aperture performance does not adequately approximate the baseline through focus mesopic aperture performance, the step parameters of the adjusted mesopic microstructure may again be adjusted. In some instances, the first through focus mesopic aperture performance may more closely approximate the baseline through focus mesopic aperture performance than does the second through focus mesopic aperture performance. In this case, the step parameters of the adjusted mesopic microstructure may be adjusted accordingly. This process may be repeated as many times as necessary in order to provide a mesopic microstructure with a through focus mesopic aperture performance that adequately approximates the baseline through focus mesopic aperture performance. Ultimately the mesopic microstructure with the through focus mesopic aperture performance that most closely approximates the baseline through focus mesopic aperture performance may be selected and implemented in the manufacturing and forming of an ophthalmic lens.

Once both the photopic microstructure and the mesopic microstructure have been selected, an ophthalmic lens may be formed and manufactured with the selected photopic microstructure in the photopic aperture of the ophthalmic lens and with the selected mesopic microstructure in the mesopic aperture of the ophthalmic lens. The ophthalmic lens may provide presbyopia-correcting full depth of focus vision.

As disclosed herein, full depth of focus IOL includes a diffractive structure formed in a surface of the IOL optic material that extends depth of focus for enhanced photopic and mesopic vision.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. An intraocular lens comprising:
an anterior optical surface and a posterior optical surface, at least one of the anterior optical surface and the posterior optical surface including a first surface region corresponding to a photopic aperture of a pupil and a second surface region corresponding to a difference between the photopic aperture and a mesopic aperture of the pupil;
a first microstructure pattern formed in the first surface region, the first microstructure pattern introducing a phase perturbation into an optical path of incoming light such that a full depth of focus for photopic vision is provided, the first microstructure pattern defined by a first step pattern; and
a second microstructure pattern formed in the second surface region, the second microstructure pattern configured to provide trifocal vision in the mesopic aperture, wherein:
the second microstructure pattern is defined by a second step pattern different from the first step pattern, the second step pattern comprising a first step having a first step height, a second step adjacent to the first step in a given direction and having a second step height, and a third step adjacent to the second step in the given direction and having a third step height;
the first, second, and third step heights are different from each other such that either:
the second step height is greater than both the first step height and the third step height; or
the second step height is less than both the first step height and the third step height.

2. The intraocular lens of claim 1, wherein the first step pattern is defined by a step height, a step width, and a phase value.

3. An intraocular lens comprising:
a first microstructure pattern formed in a first surface region of an optic zone corresponding to a photopic aperture of a pupil, the first microstructure pattern introducing a phase perturbation into an optical path of incoming light such that a full depth of focus for photopic vision is provided, the first microstructure pattern defined by a first step pattern;
a second surface region of an optic zone corresponding to a difference between the photopic aperture and a mesopic aperture of the pupil; and a second microstructure pattern formed in the second surface region, the second microstructure pattern configured to provide trifocal vision in the mesopic aperture, wherein:
the second microstructure pattern is defined by a second step pattern different form the first step pattern, the second step pattern comprising a first step having a first step height, a second step adjacent to the first step in a given direction and having a second step height, and a third step adjacent to the second step in the given direction and having a third step height;
the first, second, and third step heights are different from each other such that either:
the second step height is greater than both the first step height and the third step height; or
the second step height is less than both the first step height and the third step height.

4. The intraocular lens of claim 3, wherein the first step pattern is defined by a step height, a step width, and a phase value.

5. An intraocular lens comprising:
an anterior optical surface and a posterior optical surface, at least one of the anterior optical surface and the posterior optical surface including a first surface region corresponding to a photopic aperture of a pupil and a second surface region corresponding to a difference between the photopic aperture and a mesopic aperture of the pupil;
a first microstructure pattern formed in the first surface region, the first microstructure pattern introducing a phase perturbation into an optical path of incoming light such that a full depth of focus for photopic vision is provided, wherein:
the first microstructure pattern is defined by a first step pattern comprising a first step having a first step height, a second step adjacent to the first step in a given direction and having a second step height, and a third step adjacent to the second step in the given direction and having a third step height;
the first, second, and third step heights are different from each other such that either:
the second step height is greater than both the first step height and the third step height; or
the second step height is less than both the first step height and the third step height; and
a second microstructure pattern formed in the second surface region, the second microstructure pattern defined by a second step pattern different from the first step pattern.

6. The intraocular lens of claim 5, wherein the second microstructure pattern is configured to provide bifocal vision in the mesopic aperture.

7. The intraocular lens of claim 5, wherein the second microstructure pattern is configured to provide trifocal vision in the mesopic aperture.

8. The intraocular lens of claim 5, wherein the second step pattern is defined by a step height, a step width, and a phase value.

* * * * *